Feb. 15, 1949. E. S. BOERNER Plant Pat. 824
ROSE PLANT
Filed May 27, 1947
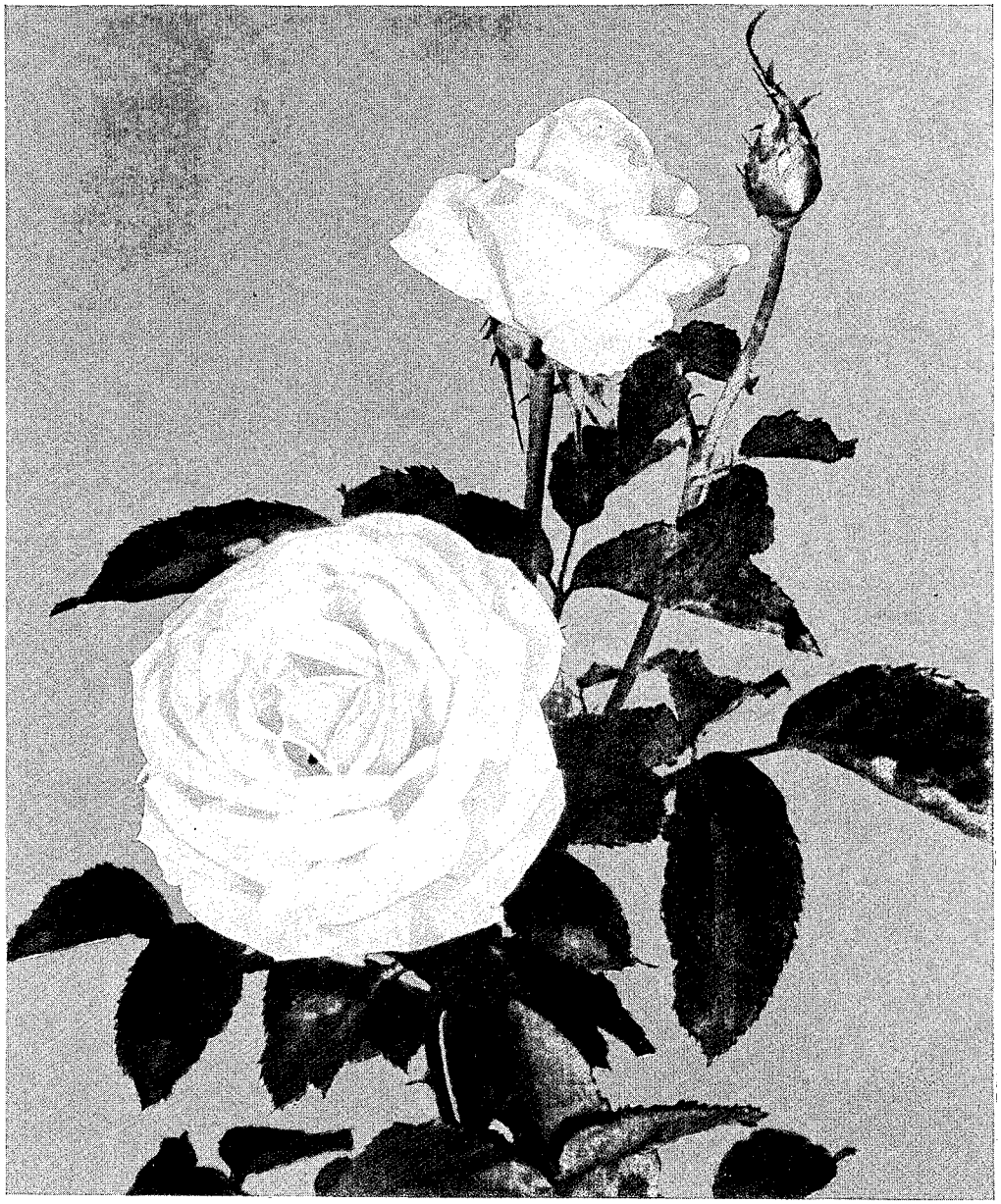
Inventor
E. S. Boerner
By Robert Robb,
Attorneys Patented Feb. 15, 1949

Plant Pat. 824

UNITED STATES PATENT OFFICE

824

ROSE PLANT

Eugene S. Boerner, Newark, N. Y., assignor to Jackson & Perkins Company, Newark, N. Y., a corporation of New York Application May 27, 1947, Serial No. 750,824

1 Claim. (Cl. 47—61)

The present invention relates to a new and distinct variety of hybrid tea rose plant, produced by crossing two very well known varieties in the yellow range of color, "Maréchal Niel" (unpatented) and "Feu Pernet-Ducher" (Pl. Pat. #103).

This new variety is a sturdy, vigorous bush plant with upright branches, heavy foliage and stately blooms. The distinctive characteristics of this variety appear more particularly in the flowers—unusually long lasting, frequently keeping for ten days; very resistant to sunburn; of an attractive color combination of yellow and pink, more specifically defined hereinafter, together with the characteristic green veining of the petals in bud and open flower.

Asexual reproduction of this new variety shows the foregoing characteristics come true to form and are established.

In the drawing are shown typical specimens of the flower at different stages of development and also of the foliage, all reduced in size.

The following is a detailed description of the new variety, color terminology being in accordance with Ridgway's Color Standards and Nomenclature:

Parentage: Seedling.
*Seed parent.*—"Maréchal Niel."
*Pollen parent.*—"Feu Pernet-Ducher."
Classification: Botanic and commercial—hybrid tea.

*Flower*

(Observations made at Newark, New York, by Jackson & Perkins Company, in the month of October.)

Blooming habit: Recurrent—continuous.
Bud:
*Size.*—Large.
*Form.*—Ovoid. Is not affected by wet or hot weather.
*Color.*—When sepals first divide—Capucine Orange, Plate 3. When petals begin to unfurl—Capucine Orange, Plate 3; two outer petals have prominent Clear Yellow Green, Plate 6, veining and irregular edge. When half blown—inside of petals—Pale Yellow Orange, Plate 3; reverse of petals—Capucine Orange, Plate 3.
*Sepals.*—Branched. Curl back when petals begin to unfurl. Color—outside: Cress Green, Plate 31; center ridge, Hay's Russet, Plate 14; inside: Light Cress Green, Plate 31; center ridge, Hay's Russet, Plate 14.
*Calyx.*—Shape—funnel. Size—broad. Aspect—smooth. Odor when rubbed—none. Color—Parrot Green, Plate 6.

*Peduncle.*—Length—long. Aspect—smooth. Color—Hessian Brown, Plate 13. Strength—erect; heavy.
*Opening.*—Opens up well. Is not affected by adverse weather conditions.
Bloom:
*Size.*—Large. Average size when fully expanded, 5".
*Borne.*—Singly and several to stem.
*Stems.*—Long; strong.
*Form.*—When first open—globular. Permanence—retains its form to the end.
*Petalage.*—Double (full but open center). Number of petals under normal conditions, 25 to 30.
*Color.*—Center of flower—Capucine Orange, Plate 3. Outer petals—Orange Pink, Plate 2; two outer petals have prominent Pale Greenish Yellow, Plate 5, veining. Base of petals (aiglet)—Lemon Chome, Plate 4. Inside of petals—Pale Yellow Orange, Plate 3; Light Orange Yellow, Plate 3, extending from the base of the petal. Reverse of petals—Orange Pink, Plate 2; edges, Light Ochraceous Buff, Plate 15. General tonality from a distance — Capucine Buff, Plate 3.
*Discoloration.*—General tonality at end of first day—Capucine Buff, Plate 3. Second day—Pale Yellow Orange, Plate 3. Third day—Pale Yellow Orange, Plate 3.
Petals:
*Texture.*—Thick. Is not affected by wet or hot weather.
*Appearance.*—Inside—shiny; outside — satiny.
*Form.*—Round.
*Arrangement.*—Imbricated (regularly arranged shingle-like). Petaloids in center—few; large.
*Persistence.*—Hang on and dry.
*Fragrance.*—Strong. Nature—"Old Rose perfume" (centifolia).
*Lasting quality.*—On the plant and as cut flower—very long.
Genital organs:
*Stamens.*—Anthers — large; few. Color—Light Cadmium, Plate 4. Arrangement—regular around styles. Filaments (threads)—long. Color—Apricot Yellow, Plate 4.
*Pollen.*—Maize Yellow, Plate 4.
*Styles.*—Bunched; uneven length; medium length; thin.
*Stigmas.*—Baryta Yellow, Plate 4.
*Ovaries.*—All enclosed in calyx.

3

*Plant*

Form: Bush.
Growth: Very vigorous; upright; branching.
Foliage: 5 to 7 leaflets.
*Size.*—Large.
*Quantity.*—Abundant.
*Color.*—New foliage—upper side—Hay's Maroon, Plate 13; under side—Van Dyke, Plate 13. Old foliage—upper side—Dark Cress Green, Plate 31; under side—Light Cress Green, Plate 31.
*Shape.*—Oval pointed.
*Texture.*—Upper side—leathery; under side—rough. Ribs and veins—prominent.
*Edge.*—Serrated (saw toothed).
*Serration.*—Single; large.
*Leaf stem.*—Light Cress Green, Plate 31. Under side—smooth.
*Stipules.*—Long; bearded.
*Disease resistance.*—Resistant.
Wood:
*New wood.*—Color—Hay's Russet, Plate 14. Bark—smooth.

4

*Old wood.*—Color—Cedar Green, Plate 6. Bark—smooth.
Thorns:
*Thorns.*—Quantity—on main stalks from base and on laterals from stalk—ordinary. Form—broad base; medium length; hooked downward. Color when young—Oxblood Red, Plate 1. Position—irregular.
*Prickles and short needles.*—On main stalks and on laterals—none.

I claim:

A new and distinct variety of rose plant, characterized as to novelty by the sturdy and vigorous growing habit with upright branches and heavy foliage; by the distinctive coloring of its flowers resistant to sunburn, and their long lasting quality, and by the characteristic green veining of the petals both in bud and open flower, substantially as shown and described.

EUGENE S. BOERNER.

No references cited.